United States Patent
Pliskin

(10) Patent No.: US 10,422,727 B2
(45) Date of Patent: Sep. 24, 2019

(54) CONTAMINANT MONITORING AND AIR FILTRATION SYSTEM

(71) Applicant: Harry Leon Pliskin, Denver, CO (US)

(72) Inventor: Harry Leon Pliskin, Denver, CO (US)

(*) Notice: Subject to any disclaimer, the term of this patent is extended or adjusted under 35 U.S.C. 154(b) by 743 days.

(21) Appl. No.: 14/822,706

(22) Filed: Aug. 10, 2015

(65) Prior Publication Data

US 2016/0041074 A1 Feb. 11, 2016

Related U.S. Application Data

(60) Provisional application No. 62/035,486, filed on Aug. 10, 2014.

(51) Int. Cl.
| | |
|---|---|
| *G01N 1/22* | (2006.01) |
| *F24F 11/30* | (2018.01) |
| *G01N 15/06* | (2006.01) |
| *F24F 1/0071* | (2019.01) |
| *F24F 110/50* | (2018.01) |

(52) U.S. Cl.
CPC ......... *G01N 1/2273* (2013.01); *F24F 1/0071* (2019.02); *F24F 11/30* (2018.01); *G01N 15/0625* (2013.01); *F24F 2110/50* (2018.01)

(58) Field of Classification Search
CPC .................. G01N 1/2273; G01N 15/0625
See application file for complete search history.

(56) References Cited

U.S. PATENT DOCUMENTS

| | | | |
|---|---|---|---|
| 3,812,370 A | 5/1974 | LaViolette | |
| 4,124,606 A | 11/1978 | Anello et al. | |
| 4,350,827 A | 9/1982 | Demler et al. | |
| 4,357,105 A | 11/1982 | Loretz | |
| 4,784,675 A | 11/1988 | Leber et al. | |
| 4,794,619 A | 12/1988 | Tregay | |
| 4,947,036 A | 8/1990 | Pokorski et al. | |
| 5,484,702 A | 1/1996 | Ludwig | |
| 6,016,689 A | 1/2000 | Bright et al. | |
| 6,125,710 A * | 10/2000 | Sharp ..................... | G01N 1/26 73/863.01 |
| 6,882,997 B1 | 4/2005 | Zhang et al. | |
| 7,125,847 B1 | 10/2006 | Sachs et al. | |
| 7,387,877 B2 | 6/2008 | Kraft | |

(Continued)

FOREIGN PATENT DOCUMENTS

WO    WO 2005/110580    11/2005

OTHER PUBLICATIONS

"Air ioniser," Wikipedia, 2014, retrieved from http://web.archive.org/web/20140904070202/http://en.wikipedia.org/wiki/Air_ioniser, retrieved on May 5, 2016, 3 pages.

(Continued)

*Primary Examiner* — Daniel S Larkin
(74) *Attorney, Agent, or Firm* — Sheridan Ross PC

(57) ABSTRACT

Devices, methods and systems for monitoring, sampling, and filtering or sanitizing the air of an environment are provided. Devices and methods including air filtering units with smart features including connectivity and reporting features are provided wherein a unit is provided to communicate with a system. Based on detected values related to air contamination and particulates entrained in the air, the system and methods are capable of performing various functions including reporting and remediation functions.

7 Claims, 8 Drawing Sheets

(56) References Cited

U.S. PATENT DOCUMENTS

| | | | |
|---|---|---|---|
| 7,445,665 | B2 | 11/2008 | Hsieh et al. |
| 7,531,363 | B2 | 5/2009 | Cole et al. |
| 7,632,459 | B2 * | 12/2009 | Lentz .................... A61L 9/20 |
| | | | 250/436 |
| 7,653,404 | B2 | 1/2010 | Maki et al. |
| 7,799,272 | B2 | 9/2010 | Garvey et al. |
| 8,230,241 | B2 | 7/2012 | Saito |
| 8,340,826 | B2 | 12/2012 | Steinberg |
| 8,608,816 | B2 | 12/2013 | Palmerton et al. |
| 8,641,488 | B1 | 2/2014 | Shvetsov et al. |
| 8,724,476 | B2 | 5/2014 | Matsuura |
| 2003/0145664 | A1 * | 8/2003 | Schwarz .................. B07C 1/00 |
| | | | 73/863.22 |
| 2006/0173580 | A1 * | 8/2006 | Desrochers ............. G01N 1/26 |
| | | | 700/276 |
| 2007/0274414 | A1 | 11/2007 | Ohara |
| 2010/0094200 | A1 | 4/2010 | Dean et al. |
| 2010/0329165 | A1 | 12/2010 | Matsuura |
| 2012/0066525 | A1 | 3/2012 | Tamura et al. |
| 2012/0127285 | A1 | 5/2012 | Ishidoshiro |
| 2012/0152040 | A1 * | 6/2012 | Calio ....................... G01N 1/26 |
| | | | 73/864.34 |
| 2013/0280108 | A1 | 10/2013 | Bearup et al. |
| 2014/0132415 | A1 * | 5/2014 | Churchvara ........... G05B 19/02 |
| | | | 340/606 |
| 2014/0165842 | A1 | 6/2014 | Bonano et al. |

OTHER PUBLICATIONS

"Air Purifier Reviews—Ratings of the Best Air Purifiers," 2014, retrieved from http://web.archive.org/web/20140811111229/http://air-purifier-ratings.org/Best_Air_Purifiers.html, retrieved on May 5, 2016, 2 pages.

"Exposing the Winix PlasmaWave 5300 Air Cleaner," 2015, retrieved from http://www.winixplasmawave5300o.com/exposing-the-winix-plasmawave-5300-air-cleaner/, retrieved on May 5, 2016, 8 pages.

"Finn HEPA UV Air Purifier," Oransi, 2014, retrieved from http://web.archive.org/web/20140915085127/http://www.oransi.com/Finn-HEPA-air-purifier-p/ovht9908.htm, retrieved on May 5, 2016, 3 pages.

"HEPA," Wikipedia, 2014, retrieved from http://web.archive.org/web/20140823075844/http://en.wikipedia.org/wiki/HEPA, retrieved on May 5, 2016, 4 pages.

"Hospital Microbiome," 2014, retrieved from http://hospitalmicrobiome.com/, retrieved on Jul. 17, 2014, 29 pages.

"IC Sentinel® Applications Guide for Healthcare Environmental Air Quality Monitoring," IC Sentinel®, 2013, 11 pages.

"PlumeSafe Turbo," Buffalo Filter LLC, 2015, retrieved from http://wvvw.buffalofilter.com/products/surgical-smoke-evacuators/plumesafe-turbo/, retrieved on May 5, 2016, 3 pages.

* cited by examiner

CONTAMINANT MONITORING AND AIR FILTRATION SYSTEM

REFERENCE TO RELATED APPLICATIONS

This U.S. Non-Provisional Patent Application claims the benefit of priority from U.S. Provisional Patent Application Ser. No. 62/035,486, filed Aug. 10, 2014, the entire disclosure of which is hereby incorporated by reference.

FIELD

The present disclosure relates to air monitoring and filtering devices and systems. More specifically, embodiments of the present disclosure relate to devices for the intake, monitoring, sampling, analysis, and filtering of air. Systems, devices, and methods further comprise the ability to analyze quantities of air and provide data and feedback to various users, such as may be useful for determining an existing type and quantity of contaminant within an area or airflow, for modeling an environment and its contaminants, and for providing predictive or forecasting features related to air or surface contamination.

BACKGROUND

Approximately 99,000 people die every year from healthcare-associated infections and are referred to as hospital-acquired infections, or HAIs. This is due partly to the fact that microbial communities develop in a hospital or other healthcare related facilities. Means to control the spread of microorganisms within hospital or other healthcare related facilities are therefore paramount.

How microbial communities persist and change in indoor environments is of immense interest to public health bodies and scientists. Recent studies show that humans alter the microbiome of a space when they begin to occupy that space. The length of time taken to demonstrate a change (e.g., on the carpet of a bedroom) can range from four to six days, suggesting that the rate of succession in a microbial community can be influenced by the way in which the occupants interact with that space. In a hospital setting, continuously admitting and discharging patients from hospital rooms creates a persistent and an ongoing problem. The building materials (e.g., HVAC system, paint, flooring type, etc.) also influence both the rate of succession in communities and the community composition.

Contrary to public expectation, the potential for contracting a microbial pathogen is highest within a hospital environment, and these infections are much more likely to be fatal. The Centers for Disease Control and Prevention identified 1.5 million cases of environmentally-contracted identifiable diseases in the United States for 2002, 15,743 of which resulted in death (1%). In comparison, during the same year, estimates of HAIs in the United States was 1.7 million, a rate of 4.5 infections per 100 hospital admissions, which contributed to an astonishing 99,000 deaths (6%). This sobering statistic places HAIs as the sixth leading cause of death, ahead of diabetes, influenza/pneumonia, and Alzheimer's. Also, the cost of extended the stay of a patient due to their contracting an HAI is quite significant.

HAIs, also referred to as nosocomial infections, are usually acquired between forty-eight hours and four days after a patient has been admitted to the hospital. Currently, 5% of patients admitted to U.S. medical facilities are affected, with the total number exceeding 1 million people with 1.7 million HAIs requiring 170 million patient days. These infections are normally viral or bacterial in origin, but fungal infections have not been ruled out. The vast majority of these cases occur while the patient is being treated for the ailment that resulted in the hospital admission in the first place. Approximately 36% of these infections could be linked to professional error, through improper attention to protocols for cleanliness in the hospital environment. While these numbers are shocking, they also highlight a considerable lack of evidence regarding both the source and development of nosocomial infections.

Microbes reside in many places and the risk of moving waste and soiled linens through hospitals or other healthcare related facilities is real. Aerosolisation happens whenever material, such as soiled linens, is agitated. For example, when waste material is thrown into a room or trash bin, or when soiled linens are thrown down a chute, aerosolisation takes place. This aerosolisation creates risk because microbes (fungi, bacteria, viruses) make up a relatively large percentage of the particulates and can be inhaled by staff, patients, and visitors. In addition, these microbes settle and attach to surfaces and to people. When people leave a room and walk down a hall, or in and out of a patient room, in and out of elevators, and generally mix with others in the facility, by so doing they cause the re-aerosolization of these particulates and microbes throughout the facility. Currently, many man-hours of labor are spent in wiping and cleaning surfaces, but most facilities cannot afford to hire and pay enough workers to properly clean all of these areas on a regular and consistent basis. If a system can clean the air before the microbes settle onto surfaces, a large amount of labor costs can be saved, and if the system can function 24/7, a great improvement in the reduction of HAIs can be achieved.

The essential point of any nosocomial infection or HAI is that hospitals can be risky places for those with suppressed immunity. A new patient will be exposed to potential pathogen infection risk during a care-related visit to a healthcare facility, and the risk will be multiplied during invasive treatments. Groups most immediately at risk include patients of advanced age, premature birth, or immunodeficiency. The latter can be developed inside the hospital due to drugs, illness, or irradiation, all of which can be a direct result of treatments. The rise in deaths related to *Clostridium difficile* and methicillin-resistant *Staphylococcus aureus* bacteraemia in the United Kingdom over the last 10 years has been shocking, with more than 10,000 deaths per year related to these HAIs. While the factors associated with the disease etymology and pathogenicity have often been explored, and intervention strategies expounded, the problem is not going away. There have, however, been regional successes that have made considerable ground in the removal of specific HAIs. Such successes have led to calls for action from the healthcare community, especially regarding a call for data to enable a reaction to existing and emerging threats.

Recent data, the first of its kind, indicates that high concentrations of microbes, particulates, and potential pathogens are present where soiled materials and waste are generated and transported to holding rooms and at the bottom of gravity chutes in hospital and healthcare settings. For example, in one study conducted at the University of Chicago Hospital, the following bacteria, some of which are potential pathogens, were found to be present in the gravity chute on the $9^{th}$ floor and in the basement gravity chute in greater than or equal to 0.7% relative abundance: Firmicutes/Bacilli/Bacillales/ . . . /*Staphylococcus*, Actinobacteria/Actinobacteria/Propionibacteriales/ . . . /*Propionibacterium*, Actinobacteria/Actinobacteria/Corynebacteriales/ . . .

/*Corynebacterium*, Firmicutes/Bacilli/Lactobacillales/ . . . /*Lactobacillus*, Firmicutes/Bacilli/Lactobacillales/ . . . /*Streptococcus*. Bacteroidetes/Cytophagia/Cytophagales/ . . . /*Hymenobacter*, Actinobacteria/Actinobacteria/Micrococcales/ . . . /*Microbacterium*, Cyanobacteria/Chloroplast, Proteobacteria/Betaproteobacteria/Burkholderiales/ . . . /*Herbaspirillum*, Firmicutes/Clostridia/Clostridiales/Lachnospiraceae, Actinobacteria/Actinobacteria/Micrococcales/ . . . /*Micrococcus*, Firmicutes/Clostridia/Clostridiales/ . . . /*Finegoldia*, Firmicutes/Bacilli/Bacillales/ . . . /*Bacillus*, Proteobacteria/Gammaproteobacteria/Pseudomonadales/ . . . /*Acinetobacter*, Proteobacteria/Betaproteobacteria/Burkholderiales/ . . . /*Massilia*, Firmicutes/Clostridia/Clostridiales/ . . . /*Anaerococcus*, and Bacteroidetes/Flavobacteria/Flavobacteriales/ . . . /*Chryseobacterium*.

These findings pose a risk factor, previously unknown and unstudied, not only in hospital and healthcare settings, but also in hospitality settings (such as motels and hotels, etc.), entertainment venues, apartment buildings, office buildings, and other settings or venues where waste and soiled items are being moved and, therefore, agitated-even if only slightly causing aerosolisation. These rooms are very often untreated, with limited or nonexistent air exchanges, and typically no air filtering. As discussed above, hospital and healthcare settings are unique in that the populace frequenting there may be vulnerable, sick, and/or compromised and are, therefore, of a particular concern. Thus, there is a need in the art for a system that can address this problem and help mitigate the risk of exposure to patients, staff, visitors, and customers in hospital and healthcare settings and other venues. A solution is needed that can track, measure, report, and treat the entire facility in an integrated, transparent manner on a 24/7 basis. Currently, there are no standards imposed on air filtration in hospitals and healthcare settings, but as more studies are done, regulations are sure to follow. The ability to monitor in real time and report on air quality will help facilities to prepare for and comply with the expected coming regulations.

Smoke evacuation systems provide a portable solution to eliminate the smoke byproduct generated during surgical procedures that use a laser or electrosurgical unit. The thermal destruction of tissue creates the smoke byproduct, referred to as a surgical plume. Surgical plumes have contents similar to other smoke plumes, including carbon monoxide, polyaromatic hydrocarbons, and a variety of trace toxic gases. As such, they can produce upper respiratory irritation, and have in-vitro mutagenic potential. Local smoke evacuation systems like the PlumeSafe® Turbo™ have been recommended by consensus organizations, and may improve the quality of the operating field. The PlumeSafe® Turbo™ employs four-stage filtering: (1) a pre filter; (2) an activated carbon filter; (3) a UPLA (Ultra Low Particulate Air) filter; and (4) a post filter. The PlumeSafe® Turbo™ cannot filter the air in a room to eliminate the broad spectrum of pathogens that can cause HAIs. It does not have the right filters for this purpose, nor the capacity to process the volume of air necessary to filter a room.

SUMMARY

Embodiments of the disclosure relate to air filtration systems. More specifically, various embodiments of the present disclosure relate to pulling air through one or more inlet openings in a unit with a fan or blower that exhausts cleaner air out of one or more exhaust openings. Air is drawn through a plurality of different filters contained within the unit.

In various embodiments, a particulate sampling device is employed to determine particulate concentration levels in the room. If the particle count exceeds a "set point", a control system will increase the speed of the one or more fans or blowers to increase flow rate and enhance filtration based on the increased need. When the particle count falls below the "set point", the control system will reduce the speed of the one or more fans or blowers as needed or desired.

In various embodiments, air filtration units comprise portable units that can be rolled, carried, or otherwise transmitted from one location to another. In other embodiments, the unit comprises a wall mounted, corner mounted, or ceiling mounted device. As used herein, the term(s) "air-monitoring unit" or "air-monitoring device" relate to devices that include, but are not limited to air filters. In some embodiments, air-monitoring units or devices comprise air filtration units. Air-monitoring units or devices, however, may also comprise air-sampling means, sanitization and disinfection means, and other devices in lieu of or in addition to air filtration.

In further embodiments, an air sampling device can in real time determine concentration levels of particulates in the air, and, based upon the levels of particulate determined, the unit can automatically change the speed of the blowers to either increase or decrease the volume of air drawn through the unit, or turn off the blowers altogether. The unit can also be configured to communicate with additional devices or features within a system. For example, an air filtration unit is contemplated as having communication features capable of automatically controlling door locks to the room when the air in the room is determined to be hazardous or not safe for people to enter. Sound absorbing material located within the unit, the design of the intake and exhaust vents, and the design of the airflow path work together to dampen the noise generated by the unit.

In other embodiments, a reporting unit is provided that generates and/or transmits reports regarding the operation of the unit to an outside agency, to a facility administrator, or to other entities. The reports may indicate a real time or minute-by-minute level of particulate in the air, and an indication of the severity of the levels through a color scheme, such as red for danger, yellow for caution, and green for acceptable levels of particulate, or other scheme(s). Reports of the present disclosure include, but are not limited to, reports provided for reading and interpretation by a user and reports that are designed to be conveyed to a database, server, or electronic means for archiving, further transmission, analysis, etc. These reports can take many forms, all of which are within the scope of the present disclosure.

U.S. Pat. No. 7,387,877 to Kraft, which is hereby incorporated by reference in its entirety, discloses a wall-mounted "biosensor unit" that may contain an air filter. Information obtained by the unit can be networked and processed to produce reports or alarms. Embodiments of the present disclosure contemplate providing such features. International Publication No. WO2005/110580 to Kang et al., which is hereby incorporated by reference in its entirety, discloses a method and system for predicting air filter conditions by determining resistance to air flow. An alarm is provided to indicate when a threshold value for airflow resistance has been exceeded. Embodiments of the present disclosure contemplate providing such features. U.S. Pat. No. 8,340,826 to Steinberg, which is hereby incorporated by reference in its entirety, discloses an energy management system in communication with a network and database. Embodiments of the present disclosure contemplate providing such features. U.S. Pat. No. 4,784,675 to Leber et al., which is hereby incorporated by reference in its entirety, discloses a cabinet assembly with a controller. Embodiments of the present disclosure contemplate providing such features. U.S. Pat. No. 7,445,665 to Hsieh et al., which is hereby incorporated by reference in its entirety, discloses a method for detecting the cleanliness of an air filter based on comparing an output control voltage to a fan with an actual airflow generated by the fan. Embodiments of the present disclosure contemplate providing such features. U.S. Pat. No. 3,812,370 to LaViolette, which is hereby incorporated by reference in its entirety, discloses a portable in-room air filter. Embodiments of the present disclosure contemplate providing such features.

The PlumeSafe® Turbo™ smoke evacuation system is hereby incorporated by reference in its entirety. Embodiments of the present invention contemplate providing some of the features found in the PlumeSafe® Turbo™ smoke evacuation system.

In certain embodiments, a connected air filtration and/or monitoring unit is provided that is connected to a control system. In such embodiments, the air-monitoring unit is not limited to any particular device(s). One of skill in the art will recognize that various devices, whether or not currently developed, may be provided with such embodiments of the present disclosure. For example, in one embodiment, a method is provided wherein an air-monitoring device takes samples of air in various rooms through a facility, such as a hospital, trauma center, ER, nursing home, etc. Data from the samples is uploaded to a local or remote server for storage, processing, transmission, and other functions. The samples and acquired data include data related to particulate levels within the collected air. As used herein, the term "particulate" generally refers to contaminants in the air. Such particulate includes, but is not limited to, bacteria, mold, infectious materials, pollutants, and any other body or contaminant entrained within a volume of air that is subject to detection, monitoring, removal, etc. Such particulate includes, but is not limited to, particles that may cause infection, illness, or contamination. Particulate also includes, however, relatively benign particles and materials such as pollutants, dust, dander, and other particles that are not known to cause health problems but are still preferably removed from an airstream or environment.

Methods of the disclosure further contemplate analyzing sampled air to identify specific types of particulate that may be present, comparing the particulate with a database of known particulates, revealing characteristics of the particulate (e.g. specific DNA or markers), to enable the tracking of or the movement or potential movement of a specific particulate. Data from the sampled air and/or analyzed particulate is uploaded to a local or remote server and is preferably analyzed for various criteria. In certain embodiments, analysis of the particulate includes a predictive analysis wherein potential spreading of certain particulate is predicted. Such predictive analysis may include a comparison of collected data with historical data or models to provide a prediction or forecast of potential further contamination.

Data and particulate analysis of the present disclosure is contemplated as: predicting a movement of bacteria or infection within a healthcare facility; identifying areas that are infected, require sanitation, or require isolation; identifying high risk or highly contaminated areas, identifying areas that are particularly ill-suited for certain patients and conditions and alerting professionals that such patients should not be exposed to such areas; characterizing risk levels by associated a level or status (e.g. low, medium, high, green, yellow, red, etc.) with an associated particulate count; generating prompts to a user including proposals or instructions to mitigate risk or prevent the spread of bacteria or infection; isolating particulates for any one or more of origin, path of travel, or preferred method of sanitation or remediation. Additionally, contemplated methods of the present disclosure include steps of helping users improve facility design by identifying problems and/or solutions associated with an existing or proposed design; proposing a frequency for taking future or additional readings; and generating reports for various purposes including, but not limited to record keeping, regulatory compliance practices, management of staff or resources, etc.

In one embodiment, a method and system is provided comprising the steps of taking an air sample, and identifying one or more particulate levels known to relate to infection or bacteria. If and when certain predetermined particulate levels are reached, a signal is provided to an air-monitoring unit such as a filter, cleaner, UV device, etc., to activate the unit or increase the power or functioning of the device in situations where the unit is already operating. Similarly, where an air-monitoring unit identifies that particulate levels are at or below a predetermined threshold level, a signal is provided to turn-off or scale down unit operations. Additionally, the detection of certain levels and/or certain particulates provides a signal to activate specific features of a unit such as UV light features, self-guided vehicles containing air-filtration devices, etc. The system may also provide prompts to a central processing unit or control station to indicate that a contamination exists and/or certain remedial actions are required.

In various embodiments, methods and systems of the present disclosure contemplate various data-collection features. For example, one or more air-monitoring units are provided and capable of measuring particulate levels in an air-space or air sample. The system contemplates general measurement of air particulate levels to determine a quantity or concentration of particulate(s) in a volume or unit of air. Specific measurements are further contemplated wherein a unit is provided to detect the presence of specific types of bacteria (for example), and/or specific DNA or markers associated with a bacteria, virus, etc. In addition to detection means, output means are further contemplated wherein the system is capable of detecting particulates as well performing or prompting various remedial actions based upon inputs from the detection means.

Although various embodiments of the present disclosure relate and describe sampling of air (i.e. fluid), additional embodiments further contemplate performing various method steps as shown and described herein wherein solid surfaces (e.g. counters, floors, trays, tools) are analyzed, associated particulates or contaminants are detected, and output means of the system are applied. For example, in certain embodiments, any one or more of the remedial actions described herein such as data analysis, storage, auto-activation of certain devices, prompting users etc., are undertaken based upon a sampling of a surface (e.g. swabbing). One of skill in the art will recognize that in various embodiments, an air-monitoring unit may be replaced with or supplemented with a device for detecting particulate or contaminants on a solid surface without deviating from the scope and spirit of the present disclosure.

In one embodiment, a method for analyzing and filtering air is provided, the method comprising the steps of providing an air-monitoring unit comprising at least one filter, an air sampling device, and a microprocessor; drawing air through an airflow path of the air-monitoring unit in communication with the microprocessor; determining a particulate count of the air entering the air-monitoring unit, the particulate count comprising at least one of bacteria, pollutants, viruses, dust and dander. The particulate count is compared to a predetermined set of stored values, the stored values comprising at least one of particulate type and particulate quantity. Data related to the particulate count is transmitted to at least one of a local server and a remote server for at least one of storage and further processing. Based on the comparing step, at least one operating parameter of the air-monitoring unit is adjusted.

In yet another embodiment, a method of analyzing and filtering air is provided, the method comprising the steps of providing an air-monitoring unit comprising at least one of a filter and an air sampling device, the air sampling device comprising means for determining particulate concentration levels in a quantity of air; drawing air through an airflow path of the air-monitoring unit; determining a particulate count of the air entering the air-monitoring unit, the particulate count comprising at least one of bacteria, pollutants, viruses, dust and dander. Comparing with the microprocessor the particulate count to a predetermined set of stored values, the stored values comprising at least one of particulate type and particulate quantity; and reporting data related to the particulate count to a remote location; and based on the comparing step, adjusting at least one operating parameter of the air-monitoring unit.

In one embodiment, a system for monitoring and filtering air is provided, the system comprising a cabinet comprising an air inlet and an air outlet, at least one filter and at least one of a fan and a blower provided within the cabinet, an air flow path extending between the air inlet and the air outlet, wherein the at least one filter is provided in the air flow path. A microprocessor is electrically connected to the at least one of a fan and a blower, and an air sampling device is electrically connected to the microprocessor. A speed control device is provided and electrically connected to the microprocessor and the at least one of a fan and a blower. The microprocessor receives information related to a particulate count determined by the air sampling device and compares the information to predetermined values, and sends signals to the speed control device to adjust the speed of the at least one of a fan and a blower based on the comparison of the particle count to the predetermined values.

Figure 1:
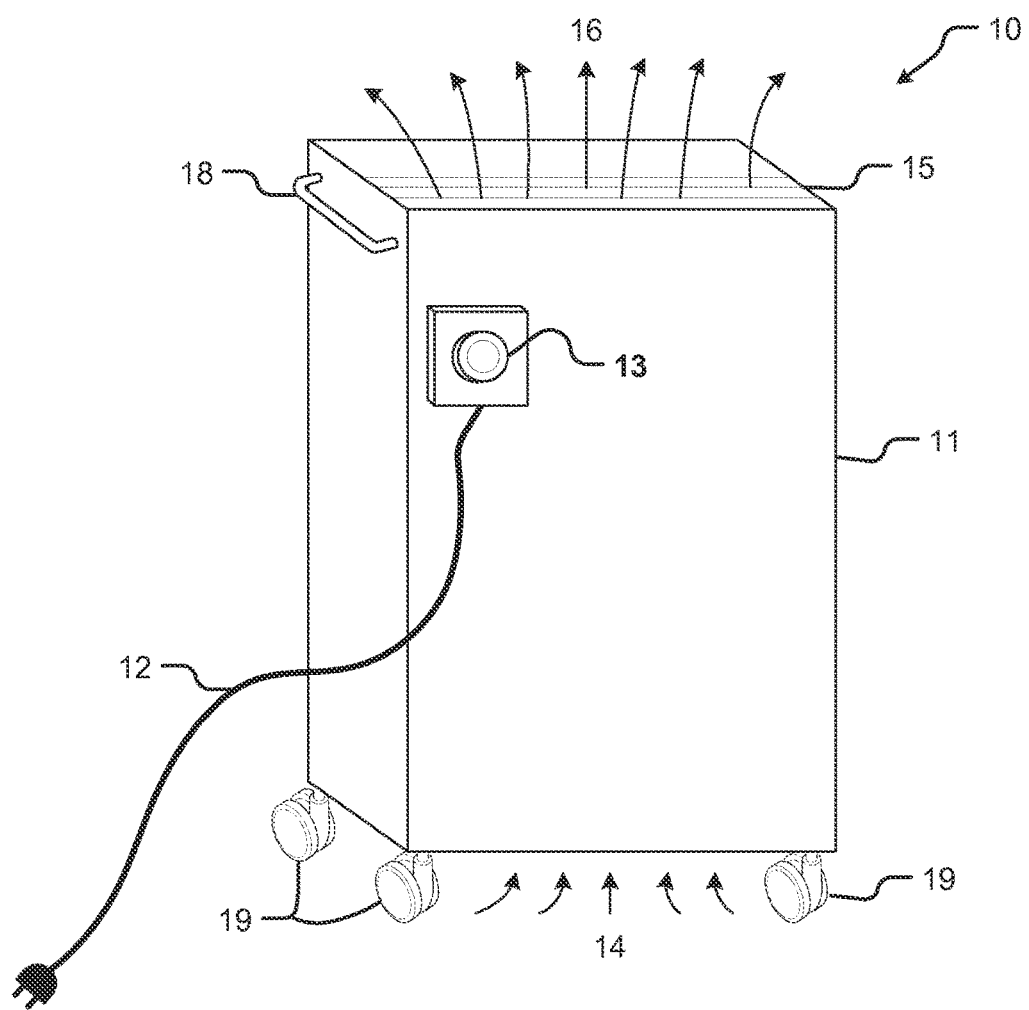
FIG. 1 shows a perspective view of one embodiment of a portable air filtration system of the present disclosure.

To assist in the understanding of the present disclosure the following list of components and associated numbering found in the drawings is provided herein:

| Table of Components | |
|---|---|
| Component | # |
| portable air filtration system | 10 |
| cabinet | 11 |
| power cord | 12 |
| speed control device | 13 |
| inlet arrows | 14 |
| exhaust vent | 15 |
| outlet arrows | 16 |
| handle | 18 |
| wheels | 19 |
| wall-mounted air filtration system | 20 |
| cabinet | 21 |
| power cord | 22 |
| speed control device | 23 |
| inlet arrows | 24 |
| exhaust vent | 25 |
| outlet arrows | 26 |
| electrical outlet | 27 |
| ceiling-mounted air filtration system | 30 |
| cabinet | 31 |
| power cord | 32 |
| speed control device | 33 |
| inlet arrows | 34 |
| exhaust vent | 35 |
| outlet arrows | 36 |
| electrical outlet | 37 |
| corner-mounted air filtration system | 40 |
| cabinet | 41 |
| power cord | 42 |
| speed control device | 43 |
| inlet arrows | 44 |
| exhaust vent | 45 |
| outlet arrows | 46 |
| electrical outlet | 47 |
| blower | 51 |
| air intake area | 52 |
| plurality of filters | 53 |
| inlet filter | 54 |
| pre-filter | 55 |
| final filter | 56 |
| air sampling device | 58 |
| microprocessor | 59 |
| sound absorption material | 60 |
| electrical power | 61 |
| hosted server | 62 |
| communications network | 64 |
| indicator lights | 65 |
| communications channel | 66 |
| door lock | 67 |
| users | 68 |
| air sampling device | 69 |
| rooms | 70-77 |
| hallway | 78 |

DETAILED DESCRIPTION

Referring now to the Figures, in which like reference numerals refer to structurally and/or functionally similar elements thereof, FIG. 1 shows a perspective view of one embodiment of a portable air filtration system of the present disclosure. Referring now to FIG. 1, a portable air filtration system 10 comprises a cabinet 11 and a plurality of wheels 19 and a handle 18 so that the portable air filtration system 10 can be easily moved from one location to another. The cabinet 11 may be made of stainless steel, plastic, or other suitable materials and may have antimicrobial coatings applied to the surfaces. Once in the location desired, power cord 12 is plugged into a power source (not shown). An interface or speed control device 13 is provided on an exterior of the system 10 and is provided for adjustment of the fan or blower speed from a lowest setting to a highest setting. In various embodiments, the speed control device 13 comprises a known dial for adjustment by a user. In alternative embodiments, the speed control device 13 comprises one or more electronic inputs, a switch or switches, and/or a binary control member, and may be located internally within cabinet 11. One or more fans or blowers (see FIG. 5) are provided inside the cabinet 11. The one or more fans or blowers draw air, represented by inlet arrows 14, into an air intake area provided on the bottom of cabinet 11. The air is drawn in an airflow path through a plurality of filters within cabinet 11 (see FIG. 5) and is exhausted out of exhaust vent 15 represented by outlet arrows 16 along the top side of cabinet 11.

Although various embodiments provided herein generally depict an airflow path wherein air is drawn into air filtration system 10 at a bottom portion of the system, it will be recognized that various alternative arrangements are also contemplated. For example, various embodiments of the present invention contemplate an air filtration system 10 wherein air is drawn in through bottom, side, top, front, and/or rear portions of the device as may be desired or required based on size, configuration, and intended use of the device, for example.

Figure 2:
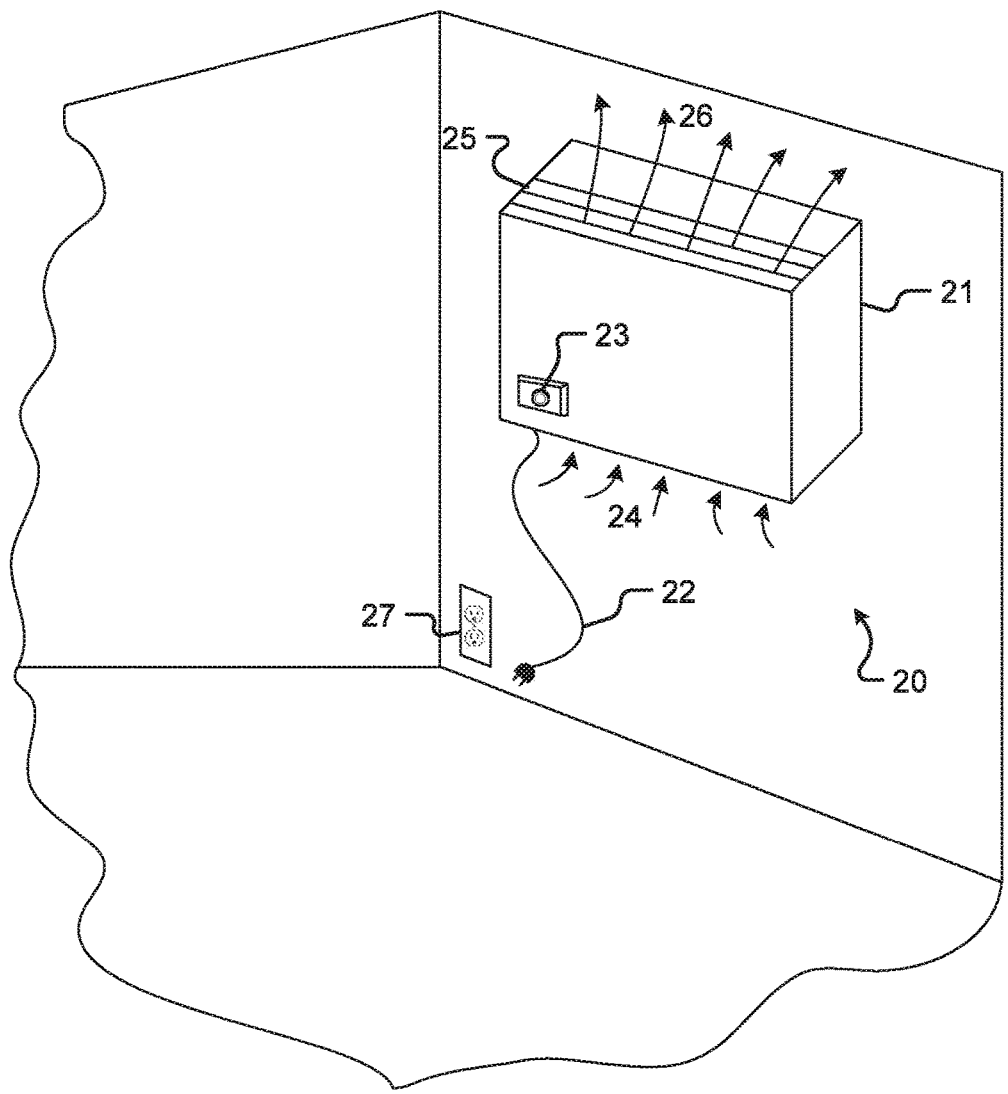
FIG. 2 shows a perspective view of one embodiment of a wall-mounted air filtration system of the present disclosure.

FIG. 2 shows a perspective view of one embodiment of a wall-mounted air filtration system of the present disclosure. Referring now to FIG. 2, a wall-mounted air filtration system 20 comprises a cabinet 21 that is mounted to a wall, and preferably a short distance below a ceiling. A power cord 22 is plugged into a power source, such as electrical outlet 27. A speed control device 23 is provided for adjustment of the fan or blower speed. One or more fans or blowers (see FIG. 5) are located inside cabinet 21. The one or more fans or blowers draw air, represented by inlet arrows 24, into an air intake area in the bottom of cabinet 21. The air is drawn through a plurality of filters within cabinet 21 (see FIG. 5) and is exhausted out of exhaust vent 25 represented by outlet arrows 26 along the top side of cabinet 21.

Figure 3:
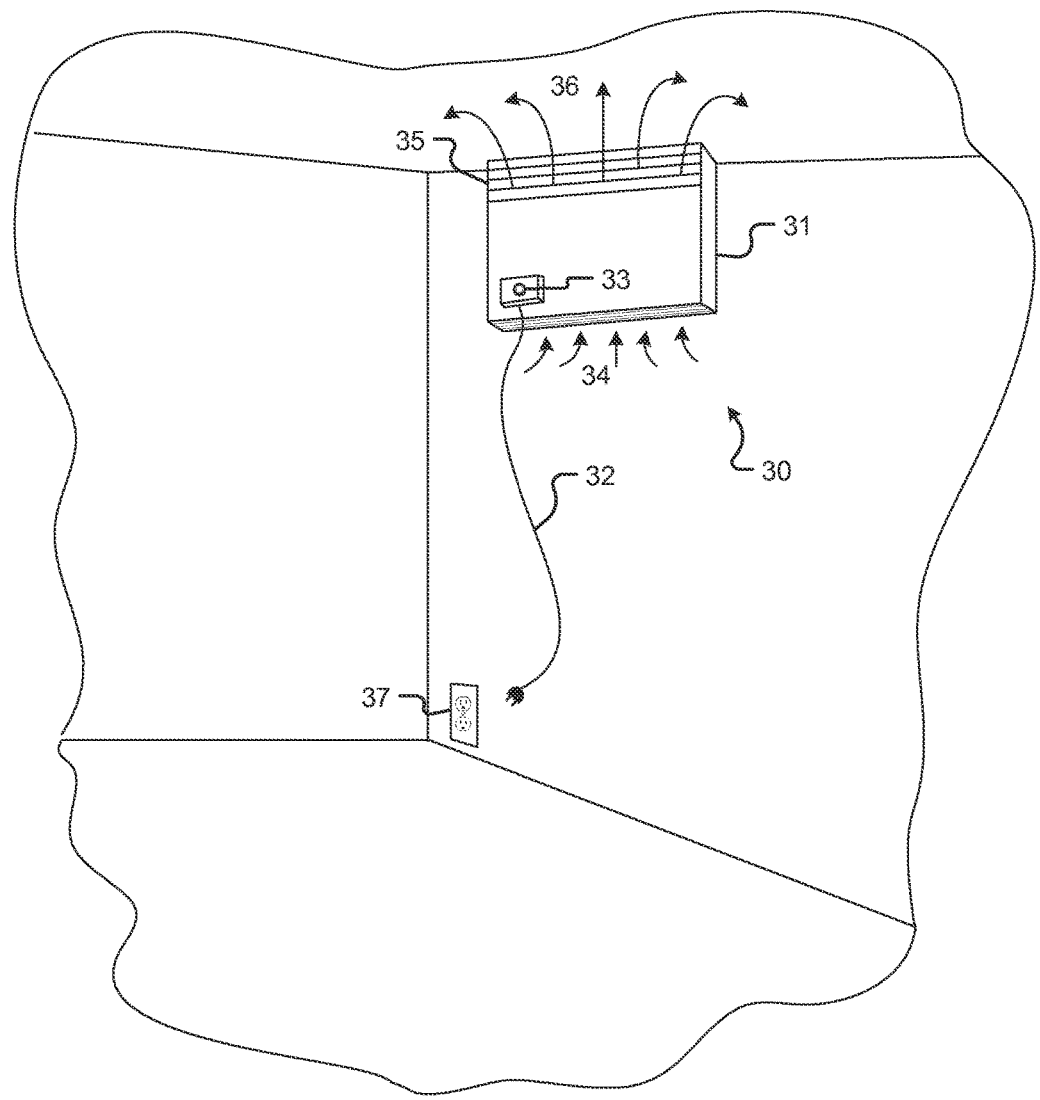
FIG. 3 shows a perspective view of one embodiment of a ceiling-mounted air filtration system of the present disclosure.

FIG. 3 shows a perspective view of one embodiment of a ceiling-mounted air filtration system of the present disclosure. Referring now to FIG. 3, ceiling-mounted air filtration system 30 has a cabinet 31 that is mounted to a ceiling. Power cord 32 is plugged into a power source, such as electrical outlet 37. Speed control device 33 can adjust the fan or blower speed from a lowest setting to a highest setting or anywhere in-between. One or more fans or blowers (see FIG. 5) are located inside cabinet 31. The one or more fans or blowers draw air, represented by inlet arrows 34, into an air intake area in the bottom of cabinet 31. The air is drawn through a plurality of filters within cabinet 31 (see FIG. 5) and is exhausted out of exhaust vent 35 represented by outlet arrows 36 along the top front side of cabinet 31 that faces out into the room. The exhaust vent 35 is oriented 90° from that shown in FIG. 2. Thus, based upon the particular room and its contents, a vertical vent 25 (FIG. 2) or a horizontal vent 35 may be employed.

Figure 4:
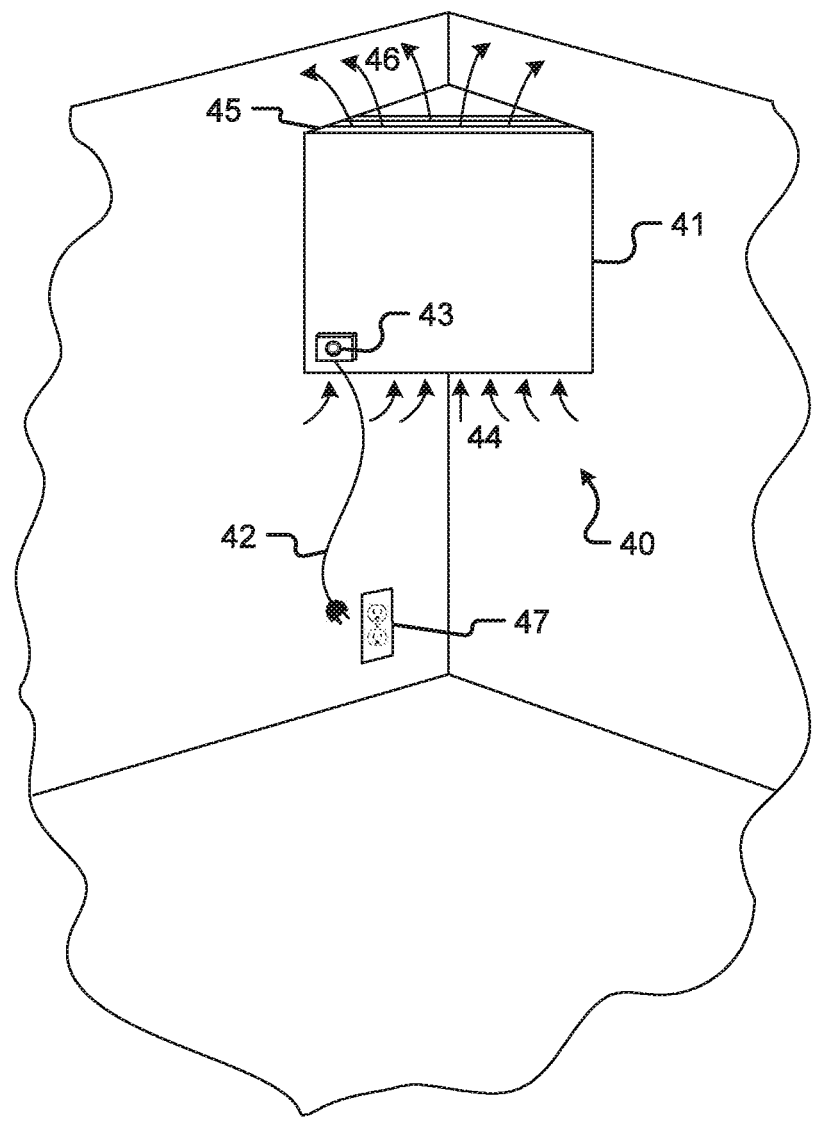
FIG. 4 shows a perspective view of one embodiment of a corner-mounted air filtration system of the present disclosure.

FIG. 4 shows a perspective view of one embodiment of a corner-mounted air filtration system of the present disclosure. Referring now to FIG. 4, corner-mounted air filtration system 40 has a cabinet 41 that is mounted to a corner of a room, typically a distance below the ceiling. Power cord 42 is plugged into a power source, such as electrical outlet 47. Speed control device 43 can adjust the fan or blower speed from a lowest setting to a highest setting. One or more fans or blowers (see FIG. 5) are located inside cabinet 41. The one or more fans or blowers draw air, represented by inlet arrows 44, into an air intake area in the bottom of cabinet 41. The air is drawn through a plurality of filters within cabinet 41 (see FIG. 5) and is exhausted out of exhaust vent 45 represented by outlet arrows 46 along the top side of cabinet 41. Corner-mounted air filtration system 40 could also be ceiling mounted like that shown in FIG. 3 with the relocation of exhaust vent 45 to the top front side of cabinet 41. Likewise, wall-mounted air filtration system 20 and ceiling-mounted air filtration system 30 could also be corner-mounted. The corner-mounted air filtration system 40 does not protrude as much into the room, and being located in a corner, it is more likely to not be in a high traffic location in the room, minimizing the risk of bumping into it.

In another embodiment, any of the air filtration systems 10/20/30/40 may be positioned in an elevator, wall, ceiling, or corner mounted, or free standing. Alternatively, the air filtration unit can be mounted on the top, bottom, or side of the elevator cab, space permitting, with the appropriate ducting to draw air into the unit and return it to the interior of the elevator cab.

Figure 5:
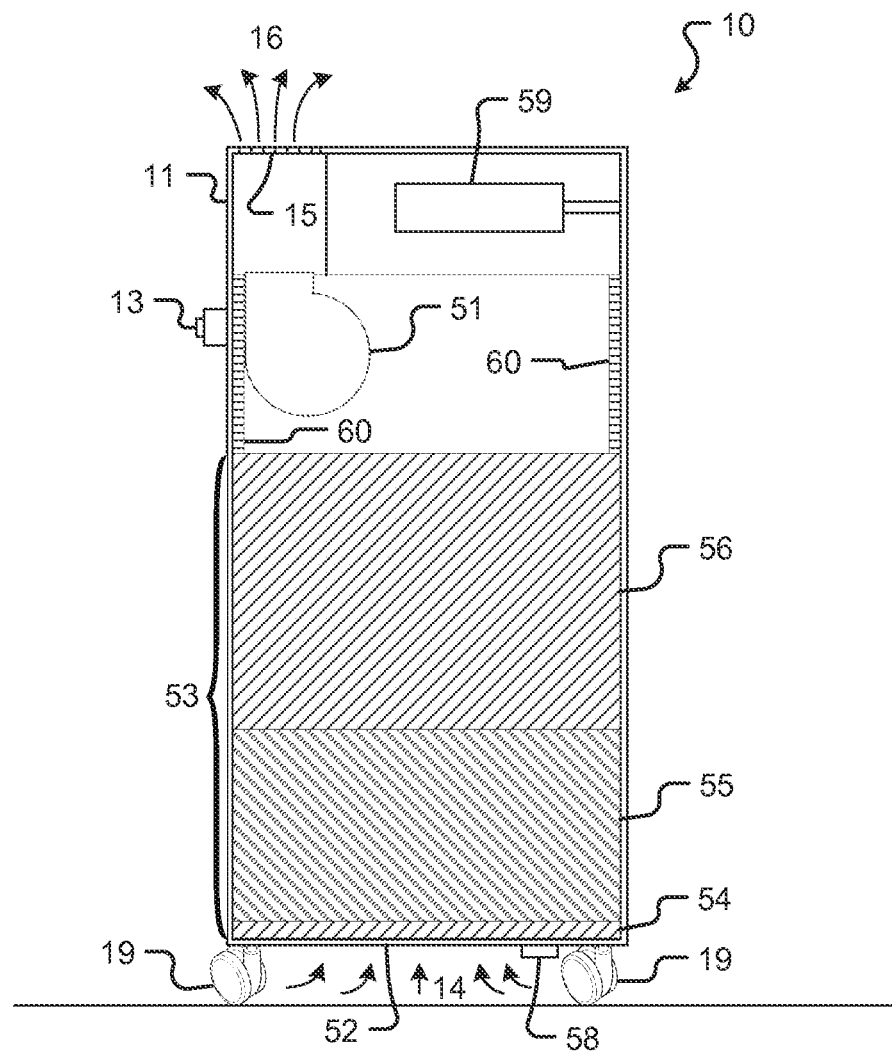
FIG. 5 shows a cross-section view of one embodiment of a portable air filtration system of the present disclosure.
Figure 6:
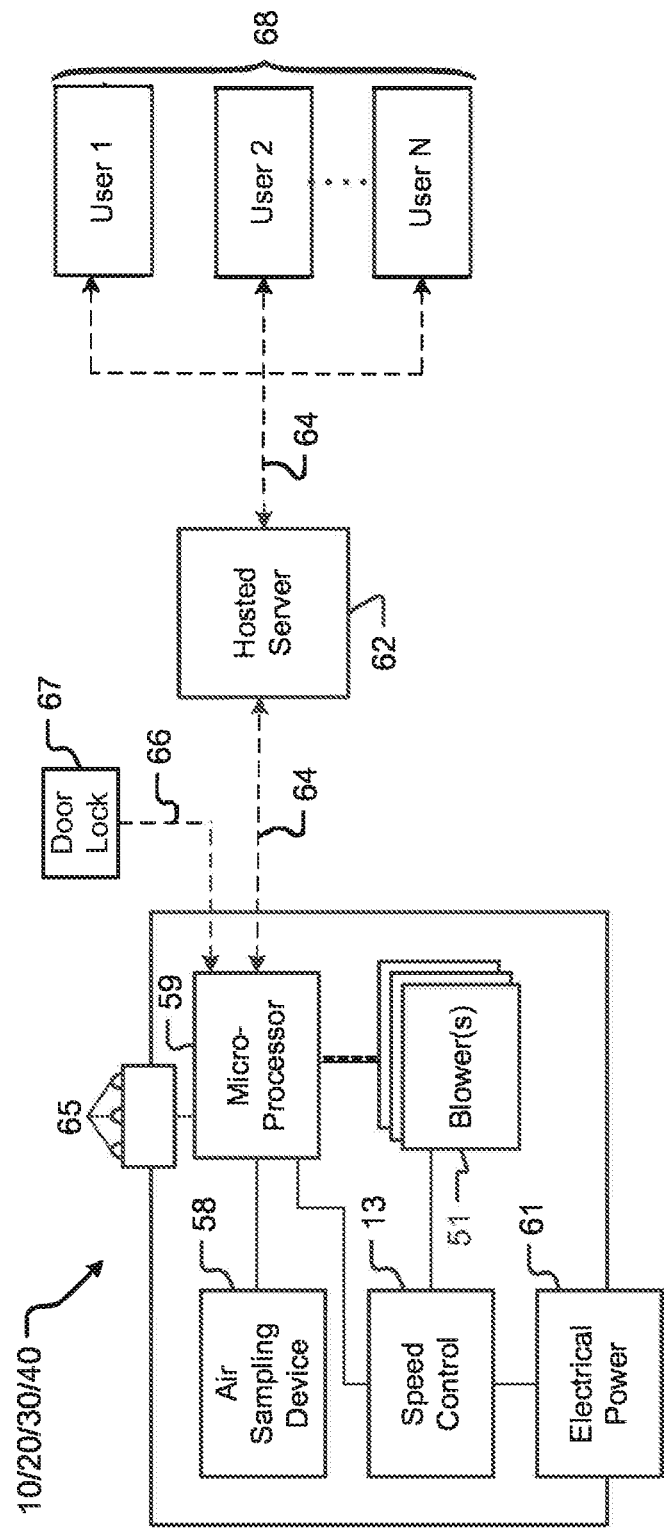
FIG. 6 shows a schematic diagram of one embodiment of a portable air filtration system of the present disclosure.

FIG. 5 shows a cross-sectional view of the embodiment of a portable air filtration system shown in FIG. 1 of the present disclosure. Referring now to FIG. 5, portable air filtration system 10 comprises a blower 51 that draws air, represented by inlet arrows 14, into an air intake area 52 in the bottom of cabinet 11. The air is drawn through a plurality of filters 53 within cabinet 11 and is exhausted out of exhaust vent 15 represented by outlet arrows 16 along the top side of cabinet 11. The plurality of filters 53 have a unique shape that attach to the interior walls of cabinet 11 in a unique manner in order to bring about the most effective seal. The plurality of filters 53 seal tightly to the interior walls of cabinet 11 for effective operation and filtration. In addition, the filters are connected to each other and sealed to the interior walls in such a way as to not allow for airflow to bypass the filters or to cause bending or breaking of the filters. This unique design provides for optimal filtering.

Inlet filter 54 is the first of the plurality of filters 53. Inlet filter 54 is a biostatic filter that inhibits the growth of fungi and bacteria and helps control microbial odors. In one embodiment, inlet filter 54 is a Flanders NaturalAire Biostatic MERV 3 (Minimum-Efficiency Reporting Value) filter, or its equivalent, and measures approximately 15 inches×24 inches by 1 inch. Air intake area 52 may be lined with copper or its alloys (brasses, bronzes, cupronickel, copper-nickel-zinc, and others) or silver. These natural antimicrobial materials have intrinsic properties to destroy a wide range of microorganisms. These and other antimicrobial coatings, such as organosilane coatings, can help to mitigate surface contamination within portable air filtration system 10.

Pre-filter 55 is the next of the plurality of filters 53. Pre-filter 55 has a high dust holding capacity. In one embodiment, pre-filter 55 is a Flanders Pleat 40 LPD (Low Pressure Drop) MERV 8 filter, or its equivalent, and measures approximately 15 inches×24 inches by 7¾ inches, having approximately 22.3 square feet of filter area.

Final filter 56 is the last of the plurality of filters 53. Final filter 56 is a HEPA (High-Efficiency Particulate Air) filter. In one embodiment, final filter 56 is an American Air Filter MEGAcel I, or its equivalent, that removes 99.99% of 0.3 micron particles, and measures approximately 12 inches×24 inches×11.5 inches.

In another embodiment, ultraviolet germicidal irradiation (UVGI) may also be incorporated into air filtration systems 10/20/30/40. UVGI has a deadly effect on micro-organisms, such as pathogens, viruses, and molds. An ultraviolet light source may be introduced into the air flow path before or after inlet filter 54, or before or after pre-filter 55, or before or after final filter 56.

Blower 51 in one embodiment comprises a FASCO 115V 60 Hz 7.8 FLA (Full Load Amp) 1750 RPM with dual eight inch direct drive blowers that deliver 1,000 cubic feet per minute (CFM) at the air intake area 52 at the bottom of cabinet 11 with a vertical cleaned air discharge. In this embodiment, blower 51 is located past the plurality of filters 53 and is thus not in the contaminated air stream. Sound absorption material 60 lines the inside of the upper portion of cabinet 11. The sound from the blower 51 is mitigated through a combination of the sound absorption material 60 and by controlling the speed of the airflow and volume of air. The air is pulled in and exhausted through exhaust vent 15 that is also sized to mitigate sound propagation.

In one embodiment, portable air filtration system 10 comprises a real time air sampling device 58 located in the air intake area in the bottom of cabinet 11. Real time air sampling device 58 determines concentration levels of particulates in the air in the room and sends the particle count to a microprocessor 59. If the particle count exceeds a "set point" microprocessor 59 will send signals to increase the speed of blower 51. When the particle count falls below the "set point" microprocessor 59 will send signals to reduce the speed of blower 51. Air sampling device 58 is typically an air sampling pump, such as the Oberon IC Sentinel®, but other methods for measuring particulates, such as color diffusion, dosimeter, and detector tubes may also be used for active sampling. Microprocessor 59 may include volatile memory and non-volatile memory upon which firmware may be stored. Software updates and operating parameter changes may be received over communications network 64 and stored.

In one embodiment, air-sampling device 58 comprises a biological analyzer that utilizes fluorescence to analyze biological particles in aerosolisation. Air-sampling devices may comprise various other particulate monitoring means as known to one of skill in the art. Biological cells typically contain fluorescent molecules, e.g., flavins, amino acids, and nicotinamide adenine nucleotides, etc., and thus emit fluorescent signals when exposed to excitation energy within a range of excitation frequencies. The particular wavelengths found in the induced fluorescence can provide information to help reveal the identity and/or class of particles that are present in the particle sample. U.S. Pat. No. 7,531,363 to Cole et al., which is hereby incorporated by reference in its entirety, discloses an analyzer for bio-particles that can collect and concentrate particles on a sample collection surface and induce fluorescence in the particles and detect and analyze the excitation frequencies. Information obtained by the unit can be networked and processed to produce reports or alarms. Embodiments of the present invention contemplate providing such features.

In another embodiment, air filtration systems 10/20/30/40 may be a larger unit having two blowers 51. Blowers 51 in this embodiment are two FASCO 115V 60 Hz ⅓HP at 1075 RPM with dual ten inch direct drive blowers that deliver 2,000 cubic feet per minute (CFM) vertical cleaned air discharge. In this embodiment, inlet filter 54 is a Flanders NaturalAire Biostatic MERV 3 (Minimum-Efficiency Reporting Value) filter, or its equivalent, and measures approximately 24 inches×48 inches by 1 inch. The pre-filter 55 is four Flanders Pleat 40 LPD (Low Pressure Drop) MERV 8 filter, or its equivalent, each measuring approximately 15 inches×24 inches by 7¾ inches, each having approximately 22.3 square feet of filter area. The final filter 56 is two American Air Filter MEGAcel I, or their equivalents, that removes 99.99% of 0.3 micron particles, and each measures approximately 24 inches×24 inches×11.5 inches.

FIG. 6 is a schematic diagram of a system according to one embodiment of the present disclosure. Referring now to FIG. 6, an air-monitoring unit including but not limited to those described herein, 10/20/30/40 receives electrical power from a power input 61. The power input may include, for example, a standard AC outlet and power cord(s) extending therefrom. In alternative embodiments, a battery is provided as the power input 61. The battery may be contained within an air-monitoring unit or provided external thereto. A speed control device 13 is provided in communication with the power input 61 and unit components, such as a blower 51 to control and adjust the operation of the component(s). In addition, a microprocessor 59 is provided to regulate system function. For example, the microprocessor 59 may automatically control the speed of a blower 51 based upon a particle count received from one or more air sampling devices 58 provided within the air monitoring unit.

In various embodiments, the microprocessor 59 communicates (i.e. sends and/or receives) collected data to and from a remote hosted server 62 via any appropriate communications network 64, such as a network using an RF router to supply information over an Internet communication system. The communication network may be any combination of circuit switched, packet switched, analog, digital, wired, and wireless communication equipment and infrastructure suitable for transmitting signals to the hosted server 62. The communication network 64 therefore may include one or more of the following: intranet, the Internet, a cellular communication system, a wireless data system, a public switched telephone network, a private telephone network, a satellite communication system or point-to-point microwave system. Depending on the particular communication network utilized, microprocessor 59 may send signals in accordance with a wireless application protocol, FCC 802.11 standards, a proprietary protocol, Bluetooth, or other types of communication protocols.

In various embodiments, the microprocessor 59 provides an alarm or other indication of high concentration levels of particulates sensed in the room. This alarm can be sent electronically as an email, a text message, etc. over communication network 64, and may be displayed to a user in visual form on a screen or monitor of a computer (including smartphones), or provided as an audio alert (or other). The alarm or indication can also manifest itself in indicator lights 65 (red for danger, yellow for caution, green for acceptable levels of particulate, and blue for clean, or any other suitable color scheme) on the air-monitoring unit and/or sending a signal over communications channel 66 to perform a function. Such functions include, but are not limited to sending a signal to a door lock 67 to effectuate locking the door(s) to the room automatically until a safe level of particulates is achieved. Communications channel 66 may be any wired or wireless communication channel suitable for this purpose. Hosted server 62 may sync up with a user 68, such as a hospital system, a regulatory body or agency such as the Joint Commission on Accreditation of Healthcare Organizations (JCAHO), to keep up to date on regulatory guidelines, standards, and applicable laws, and to report compliance to such entities. Users 68 typically utilize computers, tablets, or other mobile smart devices to access hosted server 62. Hosted server 62 may also sync up with these devices to send alerts, alarms, reports, etc. Those computers typically will include at least an output device, such as a video monitor or display, and an input device, such as a keyboard or computer mouse. Hosted server 62 may also sync up with a user 68, such as an owner or operator, to determine internal parameters and requirements for air quality, environmental control guidelines, etc. Hosted server 62 may also send preventative maintenance alarms for all hardware components (e.g., filter changing, blower maintenance, etc.) and software (e.g., software updates available, regulatory guideline changes, etc.). Software updates and changes to operating parameters (particulate levels that define the red/yellow/green alarm indicators, the fan speeds required for each level, etc.) may be downloaded from the hosted server 62 to each air-monitoring unit provided in the system via communication network 64. Data gathered by hosted server 62 can be used to generate reports to be provided to regulatory agencies as well as to internal operations departments to confirm that the relevant spaces and air quality in those spaces has been cleaned.

An example of a suitable wireless link between microprocessor 59 and hosted server 62 is a wireless Internet link provided through a cellular service provider. The data message signals are routed to the hosted server 62 based on an IP address. The hosted server 62 deciphers the incoming signals to extract the appropriate data. The hosted server 62 can determine if an air-monitoring unit has been functioning properly or not. The hosted server 62 can receive reports on speed levels and vary the speed of the blower 51 for air cleaning purposes. With information received from the air sampling device 58, hosted server 62 can determine the effectiveness of air filtration systems and air-monitoring units through readouts and reporting of graphs, such as showing minute-by-minute particulate levels sensed. This info can be sent to over communication network 64. Users 68 can also access hosted server 62 over communication network 64 to constantly monitor air-monitoring units. Users 68 typically will not, however, through use of appropriate security software, be allowed to monitor data collected on other air-monitoring units which may reside upon hosted server 62 to which they are not associated. The user interface could, but need not be, a web browser application running on a computer connected to the hosted server 62 through the Internet within the communication network 64. By designating the appropriate IP address, a user can access the hosted server 62 and view minute-by-minute operational parameters of an air-monitoring unit or device associated with the system. Additional security and authentication mechanisms may also be utilized in some circumstances.

Microprocessor 59 may use collected data and/or data received from hosted server 62 to adjust operating parameters of one or more air-monitoring devices. These operating parameters can be communicated in a binary or analog fashion and could include such actions as simply turning on or off power to air-monitoring devices, or be more sophisticated and include sending actual operating instructions to air-monitoring devices, utilizing wired and/or over the air techniques and/or protocols.

Figure 7:
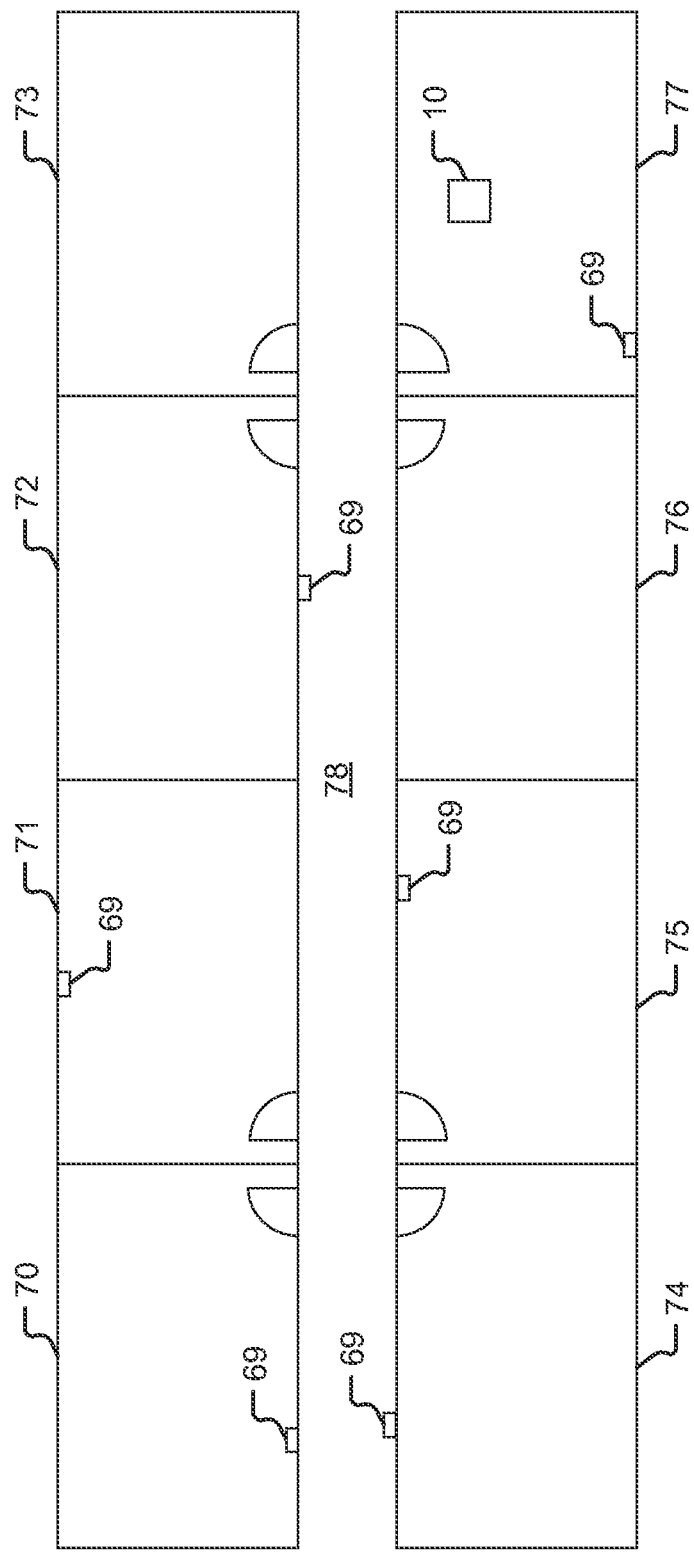
FIG. 7 shows a floor plan of a facility contemplated for use with one embodiment of the present disclosure.

FIG. 7 is a floor plan of a facility with air sampling or monitoring devices 69 in at least some of the rooms to monitor air quality and determine which room(s) require attention, sanitation, etc. and/or which rooms require an air-monitoring or filtering unit to be provided therein. In various embodiments, rooms 70-77 are provided in a hospital or healthcare related facility. The rooms may be located on the same floor or on different floors. Rooms 70, 71, 75, and 77 each have an air sampling device 69 because these rooms have been particularly identified as rooms with the potential to have very high particulate counts, such as operating rooms, patient rooms, soiled holding rooms, linen chutes, etc. Air sampling device 69 may also be located periodically along hallways, such as hallway 78. Air sampling device 69 may be battery operated or plugged into outlets in rooms 70, 71, 75, and 77 as shown in FIG. 7. In the depicted embodiment, an air-sampling device 69 in room 77 has registered the highest level of particulate count and portable air filtration system 10 has been moved into this room to filter the air. This approach helps maximize the utilization of a limited number of air filtration systems 10 (in this case, one) where there are multiple rooms that have the potential need for air filtration. Each air-sampling device 69 may have their own particulate level readout, such as the red/yellow/green scheme described above, or, may have an audible alarm to notify personnel of the need for air filtration. Alternatively, the readouts of each air-sampling device 69 may be centrally monitored through a LAN or other communication network in the hospital or healthcare facility. Alternatively, the readouts may be sent over communications network 64 to hosted server 62. Operating personnel receiving the readouts or alarms can direct that air filtration system 10 be moved to the appropriate room.

In another embodiment, air monitoring unit 10 is mounted onto a robot or mobile unit that is capable of transporting an air monitoring unit 10 or air-filtration features from room-to-room utilizing GPS or other location based technologies. Based on commands received from hosted server 62 in response to readings received from the various air-sampling devices 69, air filtration system 10 can be directed to travel to one of the rooms 70-77 or the location in hallway 78 with the most critical particulate readings.

Figure 8:
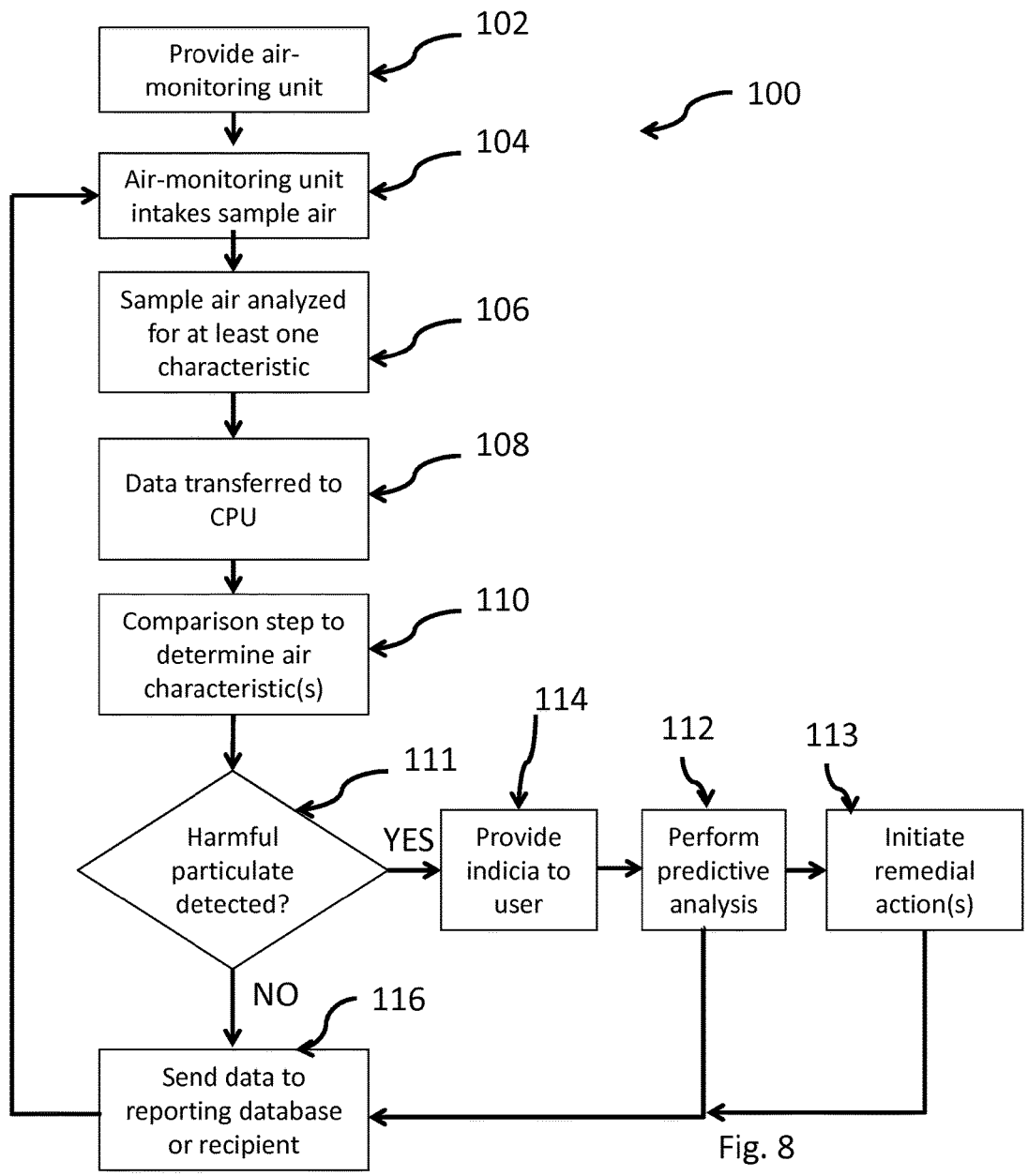
FIG. 8 is a flowchart depicting a method of monitoring an environment according to one embodiment of the present disclosure.

FIG. 8 is a flow chart of an embodiment of monitoring and attending to air quantities and infected or impacted areas according to one embodiment of the present disclosure. As shown, a method 100 is provided including a step of providing an air-monitoring unit 102, the air monitoring unit sampling the air of a surrounding environment 104 either continuously or based on a user-prompt. The air taken in is then analyzed by the features of the air-monitoring unit at step 106 to detect at least one characteristic of the air or particulates within the air. Information from sampled air is then transmitted to a central processing unit at step 108, and compared with a database of known particulates at step 110 in order to identify at least one characteristic of at least one particulate within the air including, for example, particulate type, particulate quantity, particulate concentration, etc. A decision step 111 is provided wherein the system determines whether or not a harmful particulate is present. Harmful particulates as used herein and with respect to FIG. 8 refer generally to any undesired particulate and will vary based on the environment and users' reasons and goals for monitoring the air within an environment. Harmful particulates thus include, but are not limited to, pathogens, viruses, bacteria, and any other undesired particulate matter. Where systems of the present disclosure are provided in a clean room such as those used for manufacturing silicon wafer technology, "harmful particulates" comprise simple dust particles. If no harmful particulates are detected, or a satisfactorily low level of particulates is detected in the environment, a reporting step 116 is provided to send the data to a user or database such that the data may be stored or logged, or simply acknowledged by a user. If a particulate and/or unacceptable level of particulate is detected at step 111, an indication is provided to a user at step 114, and further actions are taken by the system. For example, upon a prompt generated by the results of step 111, the system may initiate a predictive analysis step 112 and/or initiate remedial actions 113 including, for example, activating air filtration and disinfecting means, increasing the power or efficacy of existing or presently operating air filtration means, and/or other automated steps to address the contamination or infection concerns.

In the depicted embodiment, a predictive analysis step 112 is provided wherein data from the air monitoring unit is analyzed to determine a level of risk of spreading or migration of detected particulates and a predicted path or extent of such risk. The results of the predictive analysis step 112 are provided to a user through at least one of a visual and an aural output as may be provided by a computer, for example. In various embodiments, the predictive analysis step 112 comprises a step of comparing collected data from the air-monitoring unit with historical data or models to provide a prediction or forecast of potential further contamination. Such data or models may be from external sources, and/or may be built by the local system as data is stored and analyzed over time. In the latter circumstance, the data or models may be tailored for the particular environment and physical layout of the space in question, thus enhancing the accuracy and predictive power of the method. The depicted method further comprises outputting data to a user at step 114. Data output step 114 may comprise any number of formats including, for example, displaying written information on a monitor of a computing device (including smartphones), activating indicia such as lighting elements on or in connection with an air-monitoring unit, performing automated functions such as locking or closing doors, and various other outputs. Additionally, methods of the present disclosure contemplate providing a reporting step 116 wherein data (e.g. raw data) is transmitted from the system directly to a database for storage or transmission. Data may be automatically transmitted, for example, to a regulatory compliance agency in order to comply with sanitization requirements such as may be imposed upon healthcare facilities. After the data reporting step 116, a loop is provided wherein continuous monitoring is providing and with each loop beginning at step 104. The loop may be deactivated, or may be adjusted such that sampling rate is either increased or decreased. In situations wherein particulates are encountered, the method 100 may be modified such that air sampling is performed at higher frequencies.

Although FIG. 8 depicts process steps according to one method of the present disclosure, it will be recognized that additional methods are contemplated. It will also be recognized that the various process steps of FIG. 8 are provided in a sequence according to one embodiment, and that various process may be omitted or rearranged without deviating from the scope of the contemplated embodiments. For example, the step of providing indicia to a user 114 may be provided at various additional steps of the process 100, including upon an indication that no harmful particulate is present at step 111. Additionally, embodiments are contemplated wherein steps may be omitted. The step of performing a predictive analysis 112, for example, may be omitted to provide a system and method 100 that is capable of monitoring for particulates and comprises related alerts without a predictive analysis or modeling step.

What is claimed is:

1. A method for analyzing and filtering air in a hospital or a healthcare related facility, the method comprising the steps of:
   providing an air-monitoring unit in each of a plurality of rooms, each air-monitoring unit comprising at least one filter, an air sampling device, an airflow path, and a microprocessor;
   drawing air through the airflow path of each of the air-monitoring units;
   determining a particulate count of the air entering each of the air-monitoring units, the particulate count comprising at least one of bacteria, pollutants, viruses, dust and dander;
   comparing the particulate count to a predetermined set of stored values, the stored values comprising at least one of particulate type and particulate quantity;
   transmitting data related to the particulate count to at least one of a local server and a remote server for at least one of storage and further processing;
   identifying one of the plurality of rooms that comprises the highest level of particulate count;
   providing a portable air filtration system;
   moving the portable air filtration system into the room identified as comprising the highest level of particulate count; and
   adjusting an operating parameter of the portable air filtration system provided in the room identified as comprising the highest particulate count.

2. The method of claim 1, wherein adjusting the at least one operating parameter comprises a step of increasing or decreasing the speed of an air-intake fan.

3. The method of claim 1, wherein adjusting the at least one operating parameter comprises a step of increasing or decreasing an air-sampling rate.

4. The method of claim 1, further comprising a step of providing an indication to a user of the results of the comparing step.

5. The method of claim 4, wherein the indication comprises written instructions provided on a graphical user-interface.

6. The method of claim 1, wherein data related to the particulate count is electronically transmitted to a remote observer.

7. The method of claim 1, further comprising a forecasting step wherein data related to the particulate count is compared with pre-existing data related to historical data or models, and based on the comparison providing an indication to a user related to potential propagation of the contamination.

* * * * *